United States Patent [19]

Imsgard et al.

[11] Patent Number: 4,832,744
[45] Date of Patent: May 23, 1989

[54] PROCESS AND AN AGENT FOR STABILIZING TRIBUTYLTIN FUNGICIDES FOR PRESERVATION OF WOOD

[75] Inventors: Finn Imsgard; Bjorn U. Jensen, both of Kolding, Denmark

[73] Assignee: Gori A/S, Kolding, Denmark

[21] Appl. No.: 133,812

[22] PCT Filed: Apr. 9, 1987

[86] PCT No.: PCT/DK87/00036
§ 371 Date: Feb. 8, 1988
§ 102(e) Date: Feb. 8, 1988

[87] PCT Pub. No.: WO87/06176
PCT Pub. Date: Oct. 22, 1987

[30] Foreign Application Priority Data

Apr. 10, 1986 [DK] Denmark .................. 1614/86

[51] Int. Cl.$^4$ .................. C09D 5/14; C09D 5/16; C09C 143/90
[52] U.S. Cl. .................. 106/15.05; 106/18.36; 252/400.1; 252/400.52; 252/400.53; 252/400.61; 514/493
[58] Field of Search .................. 106/18.36, 15.05, 16, 106/17, 18; 252/400.52, 400.53, 400.61, 400.1; 514/493

[56] References Cited

U.S. PATENT DOCUMENTS 4,153,574  5/1979  Beiter et al. .................. 514/493
4,270,953  6/1981  Nakagawa et al. .................. 106/18
4,402,858  9/1983  Capolupo et al. .................. 524/399
4,532,161  7/1985  Collins et al. .................. 106/18
4,555,356  11/1985  Guglielmo .................. 252/400.1

FOREIGN PATENT DOCUMENTS 936340  9/1963  United Kingdom .

OTHER PUBLICATIONS

"Experiments on the degradation of tributyltin oxide: a progress report", by R. J. Orsler et al., The International Research Group on Wood Preservation, 15th Annual Meeting, SE, (1984).

*Primary Examiner*—Theodore Morris
*Attorney, Agent, or Firm*—Fleit, Jacobson, Cohn & Price

[57] ABSTRACT

Fungicides for preservation of wood, such as tributyltin oxide (TBTO) and tributyltin naphthenate (TBTN), are stabilized through inhibition of a normal autooxidation by addition of up to 1% of at least one metal salt of formula (I), wherein R is $C_4$–$C_{16}$ alkyl, aryl or alkylaryl, optionally substituted with oxygen, nitrogen, sulfur or halogen. $R_1$ is $C_1$–$C_4$ alkyl, n is 0 or 1, and Me is calcium, magnesium, nickel, zinc, copper or cadmium when n is 0, and tin when n is 1. This results in significant inhibition of the degradation of the fungicide which takes place after application to the wood so that the fungicide maintains its activity for an extended period of time.

6 Claims, No Drawings

PROCESS AND AN AGENT FOR STABILIZING TRIBUTYLTIN FUNGICIDES FOR PRESERVATION OF WOOD

The present invention concerns a process for stabilizing tributyltin fungicides for preservation of wood through inhibition of a normal autooxidation. The invention also concerns an agent for use in the performance of the process. Fungicides are extensively used for preservation of wood and other natural of synthetic materials against microbiological degradation. All organic materials are potential suppliers of carbon for biological assimilation. Fungicides are therefore widely used within agriculture, chemical industries and polymer technology to protect e.g. plants or materials, which are subject to outdoor exposure, against microbiological attacks. These attacks consist in enzymatic degradation of the organic material, and it is the task of the fungicide to provide surroundings in which the fungi generated by the degradation cannot survive. Most organic fungicides, however, are unstable because they are gradually degraded. This is often a desired process because the fungicides then do not accumulate in nature or in food products. However, preservation or protection of wood is a special phenomenon because persistent fungicides and long durability are desired. Degradation in wood can take place in several ways, e.g. under the action of light or by autooxidation. To remedy this, a plurality of various methods and agents have been proposed for stabilization of the fungicides, so that these can maintain their activity for extended periods of time.

Thus, it is proposed in the European patent application No. 83 308 to use sterically hindered amines, more particularly 2,2,6,6-tetraalkyl piperidine compounds as agents for stabilization of fungicides in surface and priming products. These compounds act as agents to protect against light. The mentioned patent application thus presupposes that the degradation process is a photooxidation, and it is demonstrated that a synergistic effect is obtained when the sterically hindered amine is used together with a UV absorbing agent. Such UV absorbing agents are preferably derivatives of 2-(2'-hydroxyphenyl)-benzotriazole or 2-hydroxybenzophenone.

It is moreover known that the wood preserving fungicide tributyltin oxide (TBTO), which is frequently used, can be protected against photooxidative degradation to the less active dibutyltin oxide by treatment with specific stabilizers, such as carboxylic acids, higher alcohols or aldehydes β see the British patent specification No. 936 340.

As mentioned above, it is not just the action of light that may cause degradation of the fungicides. As regards TBTO, it has thus been found that degradation in wood takes place entirely independently of the action of light. Initiation of the degradation process can take place by the presence of free radicals in the wood β see K. J. Orsler and G. E. Holland: Experiments on the degradation of tributyltin oxide—a progress report, The International Research Group on Wood Preservation, 15th Annual Meeting, SE (1984). It moreover appears from this report that addition of antioxidants in the form of 4-tert-butyl-catechol or 2,6-di-tert-butyl-4-methyl phenol only insignificantly impedes the degradation of TBTO in the treated wood. It is known from the SE published application No. 430 865 to use Cu or Zn salts of acetic acid and/or propionic acid as preservatives for wood, paper products, textiles and leather, and the NO published application No. 145 595 describes an agent having bactericidal and fungicidal effect and containing at least one diorganotin compound. However, the products involved are products which have bactericidal or fungicidal effect themselves, and not products whose addition stabilizes fungicides known per se.

The DE Offenlegungsschrift No. 3 224 917 describes a wood preserving agent and a process for treating wood with this agent, which contains a mixture of tris-(N-cyclohexyl-diazeniumdioxy) aluminum and bis-(tri-n-bubyltin) oxide. The two compounds are preferably mixed in a ratio of between 1:3 and 3:1, and they are separately active as wood preservatives. In combination, they have a synergistic effect. It has now surprisingly been found that an extremely good stabilization of tributyltin fungicides, such as tributyltin oxide (TBTO) and tributyltin naphthenate (TBTN), can be obtained by adding to the fungicide at least one metal salt of the general formula

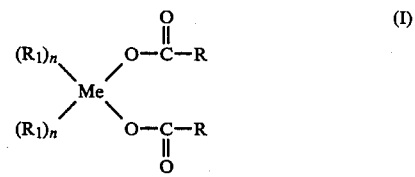

wherein R is $C_4$–$C_{16}$ alkyl, aryl or arylalkyl, optionally substituted with oxygen, nitrogen, sulfur or halogen, $R_1$ is $C_1$–$C_4$ alkyl, n is 0 or 1, and Me is calcium, magnesium, nickel, zinc, copper or cadmium when n is 0, and tin when n is 1.

The stabilizer of the above formula I is added to the fungicide in an amount of up to 1%. Salts of the above-mentioned type are used according to the U.S. Pat. No. 4,402,858 to stabilize a phosphite, serving as antioxidant, against hydrolytic degradation. These phosphites are used as antioxidants in rubber and plastics. According to the U.S. patent specification, however, a product in solution is stabilized before it is used. Further, the specification concerns stabilization of a trialkyl phosphite against hydrolysis, whereas the process of the invention serves to stabilize organic trialkyltin compounds. Such compounds are degraded in the wood by oxidative processes and not by hydrolysis. It is well-known to add ammonium compounds or organo metal compounds to TBTO and other fungicides for wood preservation. Thus, the NO Published Application No. 147 264 describes a process for treating cellulose materials by means of an organotin compound to which a monoquaternary ammonium compound has been added, and the SE published application No. 428,442 describes wood preservatives containing one or more salts of copper, nickel, zinc, cobalt, iron or manganese with organic acids. The DE Auslegeschrift No. 1 542 713 mentions a preservative for cellulose containing materials comprising as active component a pentachlorophenolate of zinc, sodium or copper, and the DE Offenlegungsschrift No. 1 961 934 mentions a wood preservative which, in addition to a neutral polymerisate, also contains e.g. zinc naphthenate or copper naphthenate. However, the prior art thus known provides agents for preserving wood and similar materials in which agents the individual components are separately biologically active.

In contrast, the object of the present invention is to stabilize the active components in fungicides so that these maintain their activity for a longer period of time. This is a general problem in connection with preservation of wood because almost all fungicides (organic molecules) in small amounts (0.02 to 0.2 kg per m³ of wood) are degraded when they are distributed in and on the wood, which is certainly not an inert material. The present stabilizers are biologically inactive in the concentrations used according to the invention, and their effect is solely to stabilize the fungicide against degradation. The amounts of stabilizing metal salts used in the process of the invention are so small that they do not have any fungicidal effect themselves. If e.g. copper naphthenate alone is used as a fungicide, about 8% of the compound has to be used if a reasonable fungicidal effect is to be obtained. In contrast, copper naphthenate in a concentration of just 0.2% is typically used in the process of the invention.

In certain products, e.g. hexamethylditin having insecticidal activity, it is desired to obtain a product stability prior to the use of the product. Thus, hexamethylditin typically loses its activity after about 3 months.

As regards wood perserving agents of the type containing tributyltin compounds, it poses no major problems to obtain stability prior to use, i.e. shelf stability. The problems of stability occurs only after the product has been applied to the wood. When this has been done, the tributyltin compound gradually degrades. This degradation can be greatly inhibited by the process of the invention. Addition of the present metal salt has the effect of inhibiting a normal autooxidation since the metal salt degrades present peroxides.

The metal salt used in the process of the invention is preferably an octoate (R is a carbon hydride with 7 C atoms). Further, it is preferred that $R_1$ is butyl.

The process of the invention provides a significantly improved stability of fungicides for preservation of wood. Tests performed as 1-year outdoor exposures and as accelerated laboratory tests have thus shown that the stability, measured as a residual content of fungicide after the test, can be increased several times when the fungicide is stabilized by the process of the invention.

The invention will be illustrated more fully by the following examples.

EXAMPLE 1

Test have been performed with an impregnating product (GORI Vac+surface treatment) in which the fungicide (TBTN) is unstabilized or stabilized with several stabilizers. The results, tabulated in table 1 below, are based on 1-year outdoor exposures (exp) and accelerated tests at the laboratory (ref.).

Gori Vac contains an oil based binder, and this binder is therefore incorporated in all formulations, unless otherwise stated.

TABLE 1

| Stabilizer | | % TBTN residue after 1 year |
|---|---|---|
| 1. Unstabilized | ref. | 17 |
| | exp. | 14 |
| 2. 0.1% Tinuvin 292 | ref. | 38 |
| (sterically hindered amine known from EP-A-83 308) | exp. | 38 |
| 3. 0.5% Zn octoate | ref. | 30 |
| | exp. | 48 |
| 4. Unstabilized without binder | ref. | 18 |
| | exp. | 25 |

TABLE 1-continued

| Stabilizer | | % TBTN residue after 1 year |
|---|---|---|
| 5. Unstabilized β binder: | ref. | 20 |
| "Hydrocarbon harts" | exp. | 16 |

This test shows that the degradation mechanism cannot be a photooxidation. Thus, it appears from the results in table 1 that the degradation of TBTN is at least of the same magnitude in the reference tests as in the outdoor tests. The reference samples have been stored in rooms with a constant temperature and degree of moisture wrapped in sheets of aluminium. It also appears that the presence of binder plays no role.

EXAMPLE 2

This example concerns testing of a plurality of compounds which are used in the process of the invention, and their stabilizing effect on tributyltin compounds (TRI) is determined.

The active fungicide is a tributyl ester or tributyltin oxide, and the tributyltin compounds are degraded in the wood to di- and monobutyltin compounds. This weakens the biological effect of the compounds, and biological activity can therefore be established in the wood.

This will probably accelerate the degradation of the tributyltin compounds.

The stabilizing effect can be affected by several factors, such as the conditions of exposure (indoor/outdoor) and the quality of the TBTN used. The stability of TBTN can probably also be affected by the origin and quality of the wood.

The results are stated in table 2 below.

In series I, wood quality and TBTN (A and B) are from the same source and therefore mutually comparable. In series IC, commercial TBTN samples from 3 different suppliers are used, the specifications being the same.

TABLE 2

| Series IA outdoor (TBTN): | |
|---|---|
| % Stabilizer | % TRI residue after 1 year |
| 1. Unstabilized | 50.5% |
| 2. 0.5% Zn—naphthenate | 58.7% |
| 3. 0.2% Cu—naphthenate | 68.0% |
| Series IB indoor (TBTN): | |
| % Stabilizer | % TRI residue after 1 year |
| 4. Unstabilized | 42.0% |
| 5. 0.5% Zn—naphthenate | 61.2% |
| Series IC outdoor: | |
| Sn—compound | % TRI residue after 1 year |
| 6. TBTN I | 39.0% |
| 7. TBTN II | 33.0% |
| 8. TBTN III | 34.0% |
| Series IIA, outdoor (TBTN): | |
| % Stabilizer | % TRI residue after 1 year |
| 9. Unstabilized | 14.0% |
| 10. 0.5% Zn—naphthenate | 48.0% |
| Series IIB indoor (TBTN): | |
| % Stabilizer | % TRI residue after 1 year |
| 11. Unstabilized | 17.0% |
| 12. 0.5% Zn—naphthenate | 30.0 |
| Series IIC outdoor: | |
| Sn—compound | % TRI residue after 1 year |
| 13. Sn—versetate | 6.0% |
| 14. Sn—linoleate | 29.0% |
| 15. TBTO | 42.0% |

It will be seen from the above results that the present metal salts have a stabilizing effect on tributyltin fungicides, and that the concentration of the stabilizer is decisive for the achievement of an optimum effect.

We claim:

1. A process for stabilizing tributyltin fungicides for preservation of wood through inhibition of a normal autooxidation, comprising adding to the fungicide at least one metal salt of the formula

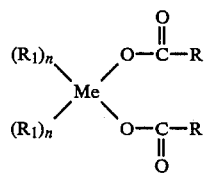
(I)

wherein R is $C_4$–$C_{16}$ alkyl, aryl or alkylaryl and is unsubstituted or substituted with oxygen, nitrogen, sulfur or halogen, $R_1$ is $C_1$–$C_4$ alkyl, n is 0 or 1, and Me is calcium, magnesium, nickel, zinc, copper or cadmium when n is 0, and tin when n is 1, said metal salt being added in an amount of no more than 1%.

2. A process according to claim 1, wherein the metal salt is an octoate.

3. A process according to claim 1, wherein $R_1$ is butyl.

4. A process according to claim 1, wherein 0.5% zinc naphthenate is added to the fungicide.

5. A process according to claim 1, wherein 0.2% copper naphthenate is added to the fungicide.

6. A stabilized fungicidal agent for preservation of wood, comprising a tributyltin fungicide and one or more metal salts of the formula

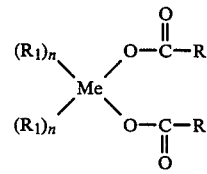
(I)

wherein R is $C_4$–$C_{16}$ alkyl, aryl or alkylaryl and is unsubstituted or substituted with oxygen, nitrogen, sulfur or halogen, $R_1$ is $C_1$–$C_4$ alkyl, n is 0 or 1, Me is calcium, magnesium, nickel, zinc, copper or cadmium when n is 0, and tin when n is 1.

* * * * *